United States Patent
Danielsson et al.

(10) Patent No.: US 11,041,968 B2
(45) Date of Patent: Jun. 22, 2021

(54) EDGE-ON PHOTON-COUNTING DETECTOR

(71) Applicant: Prismatic Sensors AB, Stockholm (SE)

(72) Inventors: Mats Danielsson, Täby (SE); Jacob J Wikner, Linköping (SE); Christer Svensson, Linköping (SE)

(73) Assignee: PRISMATIC SENSORS AB, Stockholm (SE)

( * ) Notice: Subject to any disclaimer, the term of this patent is extended or adjusted under 35 U.S.C. 154(b) by 42 days.

(21) Appl. No.: 16/653,388

(22) Filed: Oct. 15, 2019

(65) Prior Publication Data
US 2020/0158896 A1 May 21, 2020

Related U.S. Application Data

(60) Provisional application No. 62/769,121, filed on Nov. 19, 2018.

(51) Int. Cl.
| | |
|---|---|
| *H01L 27/146* | (2006.01) |
| *G01T 1/29* | (2006.01) |
| *A61B 6/00* | (2006.01) |

(52) U.S. Cl.
CPC ...... *G01T 1/2928* (2013.01); *H01L 27/14658* (2013.01); *H01L 27/14696* (2013.01); *A61B 6/4241* (2013.01)

(58) Field of Classification Search
CPC ....... G01T 1/2928; G01T 1/243; G01T 1/242; A61B 6/4241; A61B 6/4266; A61B 6/03; H01L 27/14658; H01L 27/14696
See application file for complete search history.

(56) References Cited

U.S. PATENT DOCUMENTS

| | | | |
|---|---|---|---|
| 7,170,049 B2 | 1/2007 | Iwanczyk et al. | |
| 8,183,535 B2 | 5/2012 | Danielsson et al. | |
| 2003/0173522 A1* | 9/2003 | Spartiotis | G01T 1/2928 |
| | | | 250/370.09 |
| 2005/0173774 A1* | 8/2005 | Carlson | H01L 27/14683 |
| | | | 257/461 |
| 2006/0169905 A1 | 8/2006 | Wenstrand | |
| 2006/0278943 A1 | 12/2006 | Turchetta et al. | |
| 2010/0204942 A1 | 8/2010 | Danielsson et al. | |
| 2011/0291020 A1 | 12/2011 | Iwanczyk et al. | |
| 2014/0328466 A1* | 11/2014 | Proksa | G06F 7/64 |
| | | | 378/62 |

(Continued)

FOREIGN PATENT DOCUMENTS

| | | |
|---|---|---|
| WO | 00/68710 A2 | 11/2000 |
| WO | 2020/106199 A1 | 5/2020 |

OTHER PUBLICATIONS

Mitsui et al.; Development of Integration-Type Silicon-On-Insulator Monolithic Pixel Detectors by Using a Float Zone Silicon; arXiv:1804.03338; Apr. 2018.

(Continued)

*Primary Examiner* — Kiho Kim
(74) *Attorney, Agent, or Firm* — Nixon & Vanderhye

(57) ABSTRACT

An edge-on photon-counting detector includes at least one detector module having a respective edge facing incident X-rays. The at least one detector module includes a semiconductor substrate. The edge-on photon-counting detector also includes a plurality of active integrated pixels arranged in the semiconductor substrate.

22 Claims, 14 Drawing Sheets

(56) References Cited

U.S. PATENT DOCUMENTS

| | | | | |
|---|---|---|---|---|
| 2015/0323685 A1* | 11/2015 | Nelson | ............... | G01T 1/1614 250/370.08 |
| 2017/0020475 A1 | 1/2017 | Spahn | | |
| 2017/0269238 A1 | 9/2017 | Danielsson et al. | | |
| 2018/0240842 A1* | 8/2018 | Meylan | ............... | A61B 6/4241 |
| 2018/0256121 A1 | 9/2018 | Danielsson et al. | | |
| 2018/0331137 A1 | 11/2018 | Jacob | | |

OTHER PUBLICATIONS

Fossum; Active pixel sensors: are CCDs dinosaurs?; Proceedings of SPIE; Jul. 12, 1993; vol. 1900, Charge-Coupled Devices and Solid State Optical Sensors III.

Shi et al.; An edge-on charge-transfer design for energyresolved x-ray detection; Physics in Medicine & Biology; May 18, 2016; pp. 4183-4200; vol. 61, No. 11; Institute of Physics and Engineering in Medicine.

Kleinfelder et al.; Novel Integrated CMOS Sensor Circuits; IEEE Transactions on Nuclear Science; Oct. 2004; pp. 2328-2336; vol. 51, No. 5.

Arai; Overview of SOI Pixel Development; SOIPIX; May 9, 2017; TYL-FJPPL Satellite Meeting@Strasbourg.

Burrows et al.; Active Pixel X-ray Sensor Technology Development for the Generation-X Wide-Field Imager; Astro 2010; Kavli Institute for Astrophysics and Space Research, Massachusetts Institute of Technology.

Bautz, Marshall, "Active Pixel X-ray Sensor Technology Development for the Generation-X Wide-Field Imager," A White Paper submitted to the Electromagnetic Observations from Space (EOS) Discipline Program Prioritization Panel of the Astra 2010 Astronomy and Astrophysics Decadal Survey of the National Academies.

International Search Report, dated Dec. 20, 2019, from corresponding PCT Application No. PCT/SE2019/051012.

* cited by examiner

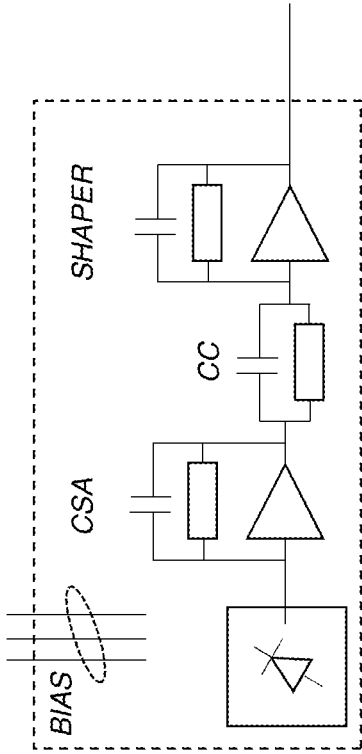
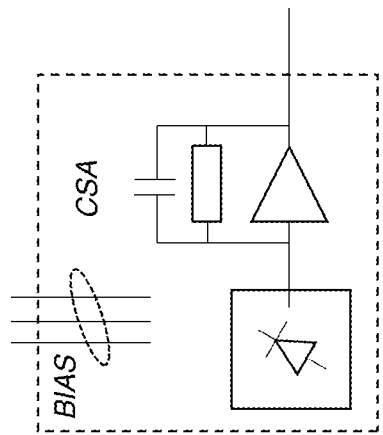
FIG. 11
FIG. 10
ANALOG READ-OUT
ELECTRONICS IN EACH PIXEL

EDGE-ON PHOTON-COUNTING DETECTOR

TECHNICAL FIELD

The present embodiments generally relate to edge-on photon-counting detectors and X-ray imaging systems comprising such edge-on photon-counting detectors.

BACKGROUND

Radiographic imaging, such as X-ray imaging, has been used for years in medical applications and for non-destructive testing. Normally, an X-ray imaging system includes an X-ray source and an X-ray detector system. The X-ray source emits X-rays, which pass through a subject or object to be imaged and are then registered by the X-ray detector system. Since some materials absorb a larger fraction of the X-rays than others, an image is formed of the subject or object.

An example of a commonly used X-ray imaging system is a Computed Tomography (CT) system. Such a CT system is based on a fan-beam geometry with an X-ray source facing an arc-shaped detector. An acquisition of a large number of X-ray projections at different angles around a patient is performed by rotating the source and the detector continuously over 360 degrees within sub-second. Both the attenuated (after the patient) and the unattenuated (before the patient) X-ray intensities are recorded, from which a 3D spatial distribution of the linear attenuation coefficients within the patient is reconstructed, accurately delineating organs and tissues.

The detector is one of the most important components of an X-ray system, including a CT system. Scintillation detectors, which consist of scintillators coupled to photodiodes, are most frequently used in modern X-ray systems. In these detectors, an interacting X-ray photon is first converted to scintillation lights in the scintillators. Electron-hole pairs are generated through the absorption of scintillation lights in photodiodes. The energy deposited by the interacting photons over a certain exposure time is integrated to obtain electrical signals output by the photodiodes that are proportional to the total 30 deposited energy. In this way, the electronic noise produced by detector elements in the detector and readout electronics is also integrated into the output signals that are transmitted to the data processing system via analog to digital converting application-specific integrated circuits (ASICs) for image reconstruction.

Photon-counting detectors that may be used in the next generation X-ray and CT imaging systems work in a totally different way as compared to the energy-integrating detectors. Incident X-ray photons are directly transferred to electrical pulses with pulse amplitudes proportional to the photon energies. These electrical pulses are then fed into the corresponding ASIC channels. Each ASIC channel typically contains a charge-sensitive pre-amplifier, a pulse shaper, a number of pulse-height comparators and counters. After being amplified and shaped, each electrical pulse is compared to a number of programmable thresholds and classified according to its pulse-height, and the corresponding counter is incremented.

Compared to the energy-integrating detectors, photon-counting detectors have the following advantages. Firstly, electronic noise that is integrated into the signal by the energy-integrating detectors can be rejected by setting the lowest energy threshold above the noise floor in the photon-counting detectors. Secondly, material decomposition, by which different components in the examined patient can be identified and quantified, is ready to be implemented by using the energy information extracted by the detector. Thirdly, more than two basis materials can be used, which benefits decomposition techniques, such as K-edge imaging whereby distribution of contrast agents, e.g., iodine or gadolinium, are quantitatively determined. Last but not least, higher spatial resolution can be achieved by using smaller pixel size. Compared to the typical pixel size of 1 $mm^2$ of current energy-integrating detectors, photon-counting detectors usually use sub square millimeter pixel size. For instance, a silicon-strip photon-counting detector can have a pixel size of 0.2 $mm^2$.

The most promising materials for photon-counting X-ray detectors are cadmium telluride (CdTe), cadmium zinc telluride (CZT) and silicon. CdTe and CZT are employed in several photon-counting spectral CT projects for the high absorption efficiency of high-energy X-rays used in clinical CT. However, these CT projects are slowly progressing due to several drawbacks of CdTe/CZT. CdTe/CZT have low charge carrier mobility, which causes severe pulse pileup at flux rates ten times lower than those encountered in clinical practice. One way to alleviate this problem is to decrease the pixel size, whereas it leads to increased spectrum distortion as a result of charge sharing and K-escape. Also, CdTe/CZT suffer from charge trapping, which would lead to polarization that causes a rapid drop of the output count rate when the photon flux reaches above a certain level.

In contrast, silicon has higher charge carrier mobility and is free from the problem of polarization. The mature manufacturing process and comparably low cost are also its advantages. But silicon has limitations that CdTe/CZT do not have. Silicon sensors must be very thick to compensate for its low stopping power. Typically, a silicon sensor needs a thickness of several centimeters to absorb most of the incident photons, whereas CdTe/CZT need only several millimeters. On the other hand, the long attenuation path of silicon also makes it possible to divide the detector into different depth segments that are read out individually. This in turn increases the detection efficiency and makes a silicon-based photon-counting detector possible to properly handle the high fluxes in CT.

Physics in Medicine & Biology (2016) 61: 4183-4200 discloses a spectral sensing detector concept using a charge-coupled device (CCD) based charge transfer scheme. The electrodes of the detector are dynamically grouped to collect energy sensitive data and compute spectrally specific line integrals.

U.S. Pat. No. 7,170,049 relates to a photon-counting mode detector based on a pixelated cadmium zinc telluride (CZT) detector having a plurality of pixels, wherein each of the pixels is used for detecting the radiation. The detector also includes a Ball Grid Array (BGA) package having a plurality of solder balls formed on a first side and a plurality of contacts formed on a second side. The BGA package also has a cavity, in which at least one integrated circuit (IC) chip is mounted. The IC chip has a plurality of readout channels, each of the readout channels being coupled to a corresponding one of the pixels via a corresponding one of the solder balls to receive an electrical signal corresponding to the radiation detected by the corresponding one of the pixels.

SUMMARY

The present embodiments generally relate to edge-on photon-counting detectors and X-ray imaging systems comprising such edge-on photon-counting detectors.

An aspect of the invention relates to an edge-on photon-counting detector. The edge-on photon-counting detector comprises at least one detector module having a respective edge facing incident X-rays. The at least one detector module comprises a semiconductor substrate. The edge-on photon-counting detector also comprises a plurality of active integrated pixels arranged in the semiconductor substrate.

Preferably, the edge-on photon-counting detector comprises active integrated pixels that may be configured to operate as detector elements and also perform analog processing of the electrical signals of the detector elements. This is a novel and unique feature for constructing edge-on photon-counting detectors.

Another aspect of the invention relates to an X-ray imaging system comprising an edge-on photon-counting detector according to the embodiments.

The present invention provides improvements over prior art X-ray detectors by using active integrated pixels in the detector modules. This means that part of the processing of the electric signals may be moved from associated processing circuitry, such as ASICs, into the pixels. This integration of at least part of the signal processing in the pixels enables smaller pixel sizes, reduction in power consumption per pixel and reduction of the minimum noise threshold.

BRIEF DESCRIPTION OF THE DRAWINGS

The embodiments, together with further objects and advantages thereof, may best be understood by making reference to the following description taken together with the accompanying drawings, in which:

FIG. 10 is a schematic diagram of an active integrated pixel according to an embodiment;

FIG. 11 is a schematic diagram of an active integrated pixel according to another embodiment;

DETAILED DESCRIPTION

The present embodiments generally relate to edge-on photon-counting detectors and X-ray imaging systems comprising such edge-on photon-counting detectors.

Figure 1:
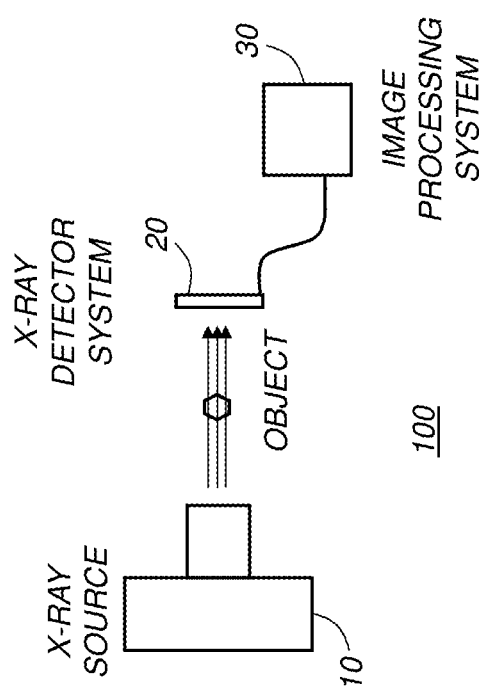
FIG. 1 is a schematic block diagram of an X-ray imaging system according to an embodiment.

It may be useful with a brief overview of an illustrative overall X-ray imaging system with reference to FIG. 1. In this illustrative, but non-limiting, example the X-ray imaging system 100 basically comprises an X-ray source 10, an X-ray detector system 20 and an associated image processing system or device 30. In general, the X-ray detector system 20 is configured to register radiation from the X-ray source 10, which optionally has been focused by optional X-ray optics and passed an object, a subject 30 or a part thereof. The X-ray detector system 20 is connectable to the image processing system 30 via suitable analog and read-out electronics, which is at least partly integrated in the X-ray detector system 20, to enable image processing and/or image reconstruction by the image processing system 30.

Figure 2:
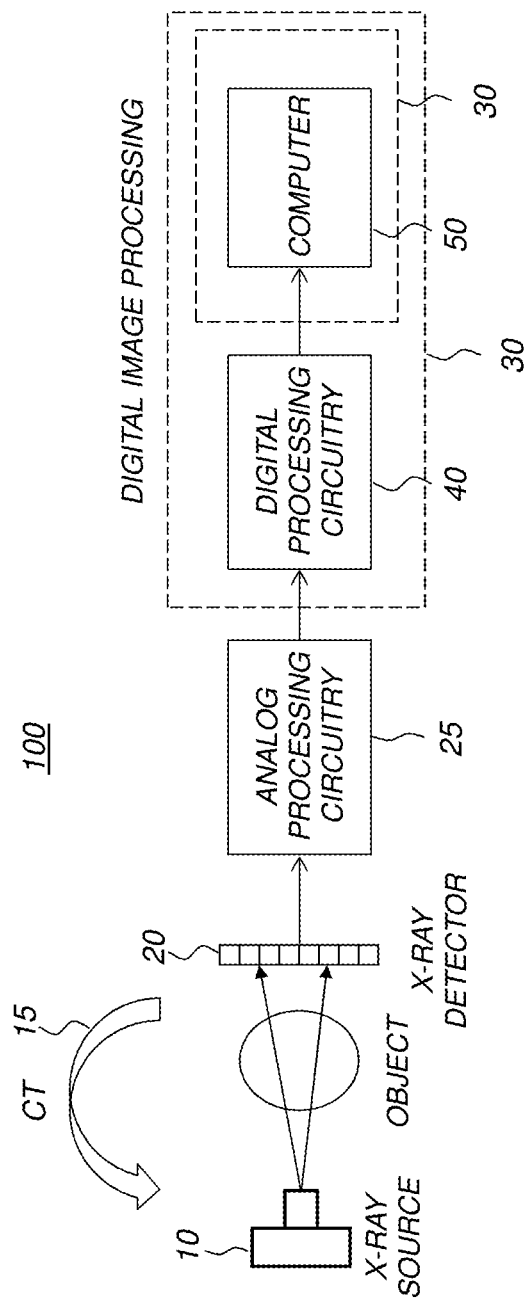
FIG. 2 is a schematic block diagram of an X-ray imaging system according to another embodiment.

FIG. 2 is a schematic diagram illustrating an example of an X-ray imaging system 100 comprising an X-ray source 10, which emits X-rays, an X-ray detector system 20 with an edge-on photon-counting detector, which detects the X-rays after they have passed through the object, analog processing circuitry 25, which processes the raw electrical signal from the edge-on photon-counting detector and digitizes it, digital processing circuitry 40, which may carry out further processing operations on the measured data, such as applying corrections, storing it temporarily, or filtering, and a computer 50, which stores the processed data and may perform further post-processing and/or image reconstruction. According to the invention, all or part of the analog processing circuitry 25 may be implemented in the X-ray detector system 20.

The overall edge-on photon-counting detector may be regarded as the X-ray detector system 20, or the X-ray detector system 20 combined with the associated analog processing circuitry 25.

The digital part including the digital processing circuitry 40 and/or the computer 50 may be regarded as the image processing system 30, which performs image reconstruction based on the image data from the edge-on photon-counting detector. The image processing system 30 may, thus, be seen as the computer 50, or alternatively the combined system of the digital processing circuitry 40 and the computer 50, or possibly the digital processing circuitry 40 by itself if the digital processing circuitry is further specialized also for image processing and/or reconstruction.

Figure 3:
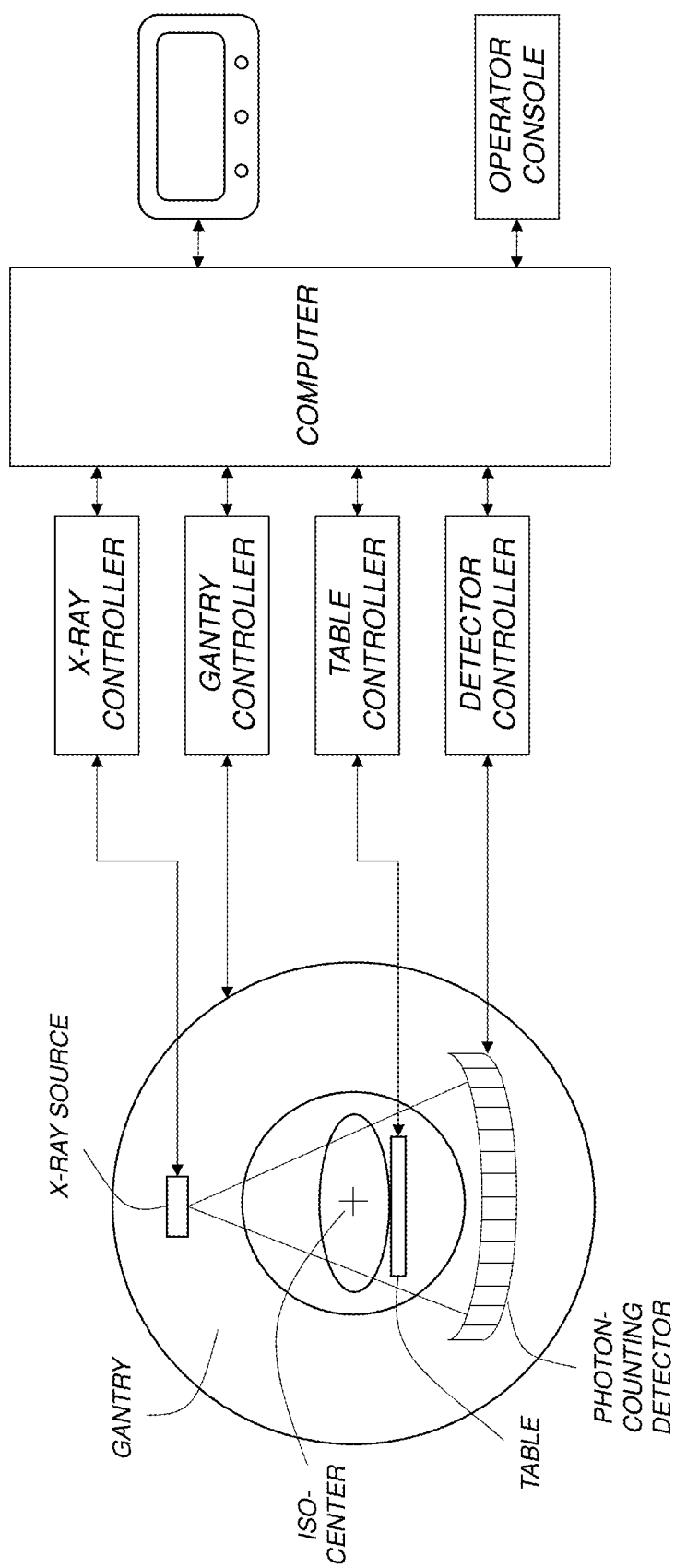
FIG. 3 is a schematic block diagram of an X-ray imaging system according to a further embodiment.

FIG. 3 is a schematic block diagram of a CT system as an illustrative example of an X-ray imaging system. The CT system comprises a computer receiving commands and scanning parameters from an operator via an operator console that has a display and some form of operator interface, e.g., keyboard and mouse. The operator supplied commands and parameters are then used by the computer to provide control signals to an X-ray controller, a gantry controller and a table controller. To be specific, the X-ray controller provides power and timing signals to the X-ray source to control emission of X-rays onto the object or patient lying on the table. The gantry controller controls the rotational speed and position of the gantry comprising the X-ray source and the edge-on photon-counting detector. The table controller controls and determines the position of the patient table and the scanning coverage of the patient.

In an embodiment, the computer also performs post-processing and image reconstruction of the image data output from the edge-on photon-counting detector. The computer thereby corresponds to the image processing system as shown in FIGS. 1 and 2. The associated display allows the operator to observe the reconstructed images and other data from the computer.

The X-ray source arranged in the gantry emits X-rays. An X-ray detector, in the form of an edge-on photon-counting detector, detects the X-rays after they have passed through the patient. The edge-on photon-counting detector is formed by plurality of pixels, also referred to as sensors or detector elements, and the associated processing circuitry, such as ASICs, arranged in detector modules. At least a portion of the analog processing part is implemented in the pixels, whereas any remaining processing part is implemented in, for instance, the ASICs. In an embodiment, the ASICs digitize the analog signals from the pixels. The ASICs may also comprise a digital processing part, which may carry out further processing operations on the measured data, such as applying corrections, storing it temporarily, and/or filtering. During a scan to acquire X-ray projection data, the gantry and the components mounted thereon rotate about an isocenter.

Edge-on is a design for a photon-counting detector, where the x-ray sensors such as x-ray detector elements or pixels are oriented edge-on to incoming x-rays.

For example, the photon-counting detector may have pixels in at least two directions, wherein one of the directions of the edge-on photon-counting detector has a component in the direction of the X-rays. Such an edge-on photon-counting detector is sometimes referred to as a depth-segmented photon-counting detector, having two or more depth segments of pixels in the direction of the incoming X-rays.

Alternatively, the pixels may be arranged as an array (non-depth-segmented) in a direction substantially orthogonal to the direction of the incident x-rays, and each of the pixels may be oriented edge-on to the incident x-rays. In other words, the photon-counting detector may be non-depth-segmented, while still arranged edge-on to the incoming x-rays.

In order to increase the absorption efficiency, the edge-on photon-counting detector can accordingly be arranged edge-on, in which case the absorption depth can be chosen to any length, and the edge-on photon-counting detector can still be fully depleted without going to very high voltages.

Photon-counting detectors have emerged as a feasible alternative in some applications; currently those detectors are commercially available mainly in mammography. The photon-counting detectors have an advantage since in principle the energy for each X-ray can be measured, which yields additional information about the composition of the object. This information can be used to increase the image quality and/or to decrease the radiation dose.

Compared to the energy-integrating systems, photon-counting CT has the following advantages. Firstly, electronic noise that is integrated into the signal by the energy-integrating detectors can be rejected by setting the lowest energy threshold above the noise floor in the photon-counting detectors. Secondly, energy information can be extracted by the photon-counting detector, which allows improving contrast-to-noise ratio by optimal energy weighting and which also allows so-called material basis decomposition, by which different materials and/or components in the examined subject or object can be identified and quantified, to be implemented effectively. Thirdly, more than two basis materials can be used, which benefits decomposition techniques, such as K-edge imaging whereby distribution of contrast agents, e.g. iodine or gadolinium, are quantitatively determined. Fourth, there is no detector afterglow, meaning that high angular resolution can be obtained. Last but not least, higher spatial resolution can be achieved by using smaller pixel size.

Figure 4:
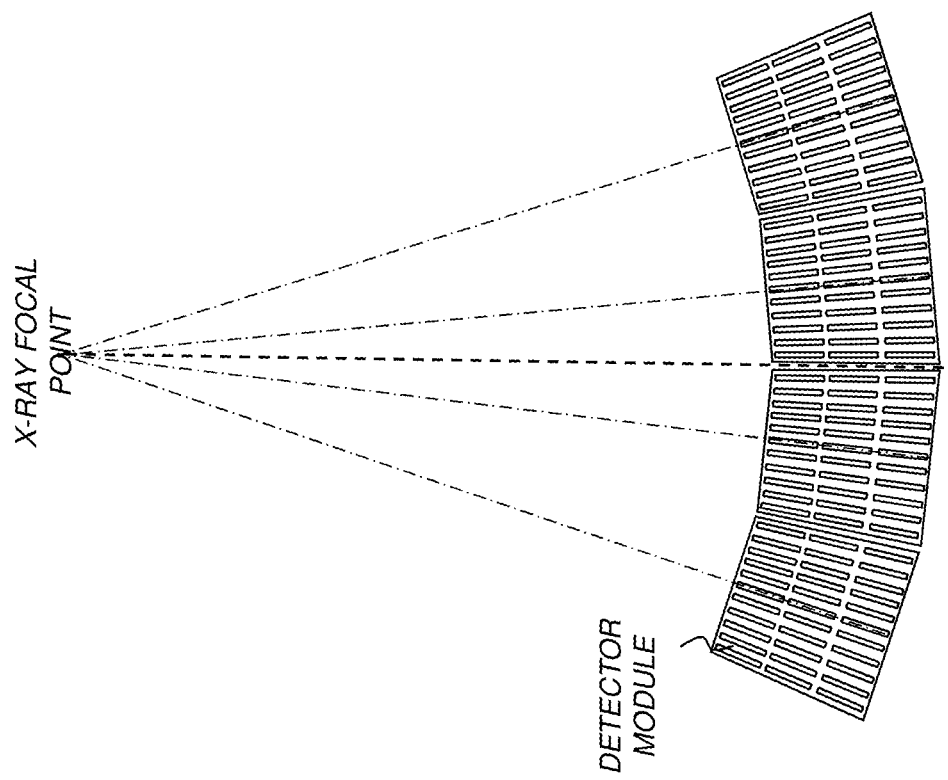
FIG. 4 is a schematic diagram of an edge-on photon-counting detector according to an embodiment.
Figure 5:
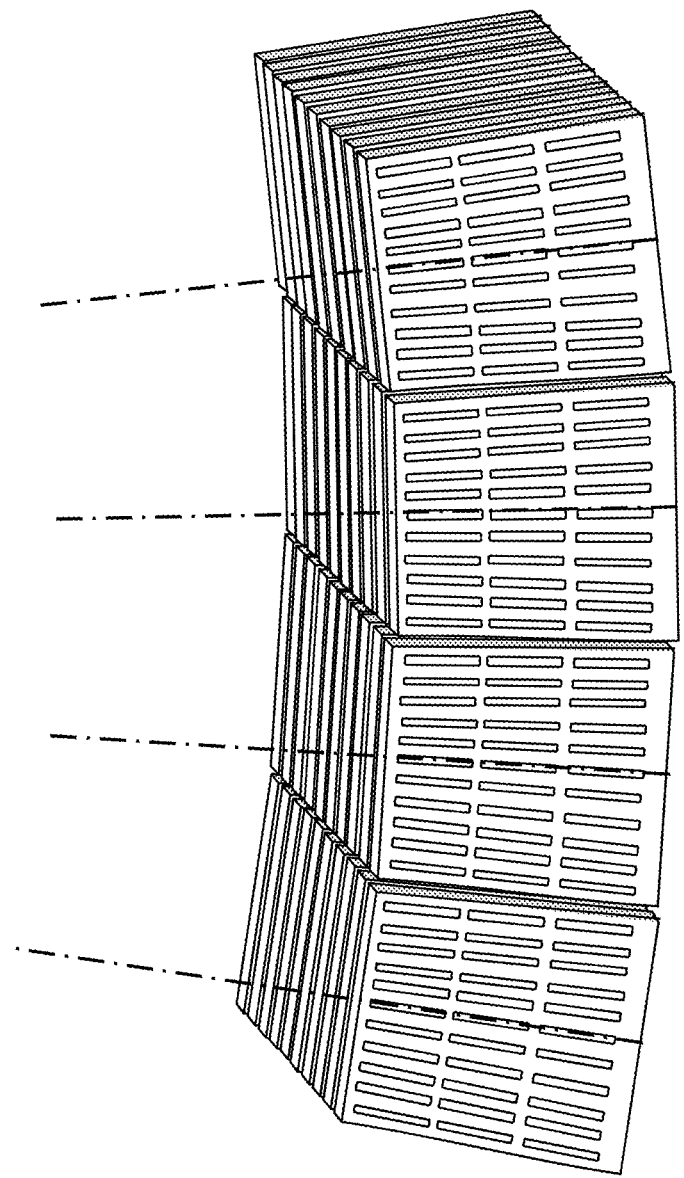
FIG. 5 is a schematic diagram of an edge-on photon-counting detector according to another embodiment.

The X-ray detector of the embodiments is an edge-on photon-counting detector comprising one or multiple, i.e., at least two, detector modules, i.e., being a modular X-ray detector. FIG. 4 is a schematic diagram of an edge-on photon-counting detector according to an exemplary embodiment. The detector modules are preferably arranged side-by-side, e.g., in a slightly curved overall geometry with respect to an X-ray source located at an X-ray focal point. FIG. 5 is a schematic diagram of an edge-on photon-counting detector with a number of detector modules arranged side-by-side and also stacked one after the other. The detector modules may be stacked one after the other to form larger sets or groups of detector modules that may be assembled together side-by-side to build up an overall edge-on photon-counting detector.

More information on so-called edge-on photon-counting detectors in general can be found, e.g. in U.S. Pat. No. 8,183,535, which discloses an example of an edge-on photon-counting detector. In U.S. Pat. No. 8,183,535, there are multiple semiconductor detector modules arranged together to form an overall detector area, where each semiconductor detector module comprises an X-ray sensor oriented edge-on to incoming X-rays and connected to integrated circuitry for registration of X-rays interacting in the X-ray sensor.

Figure 6:
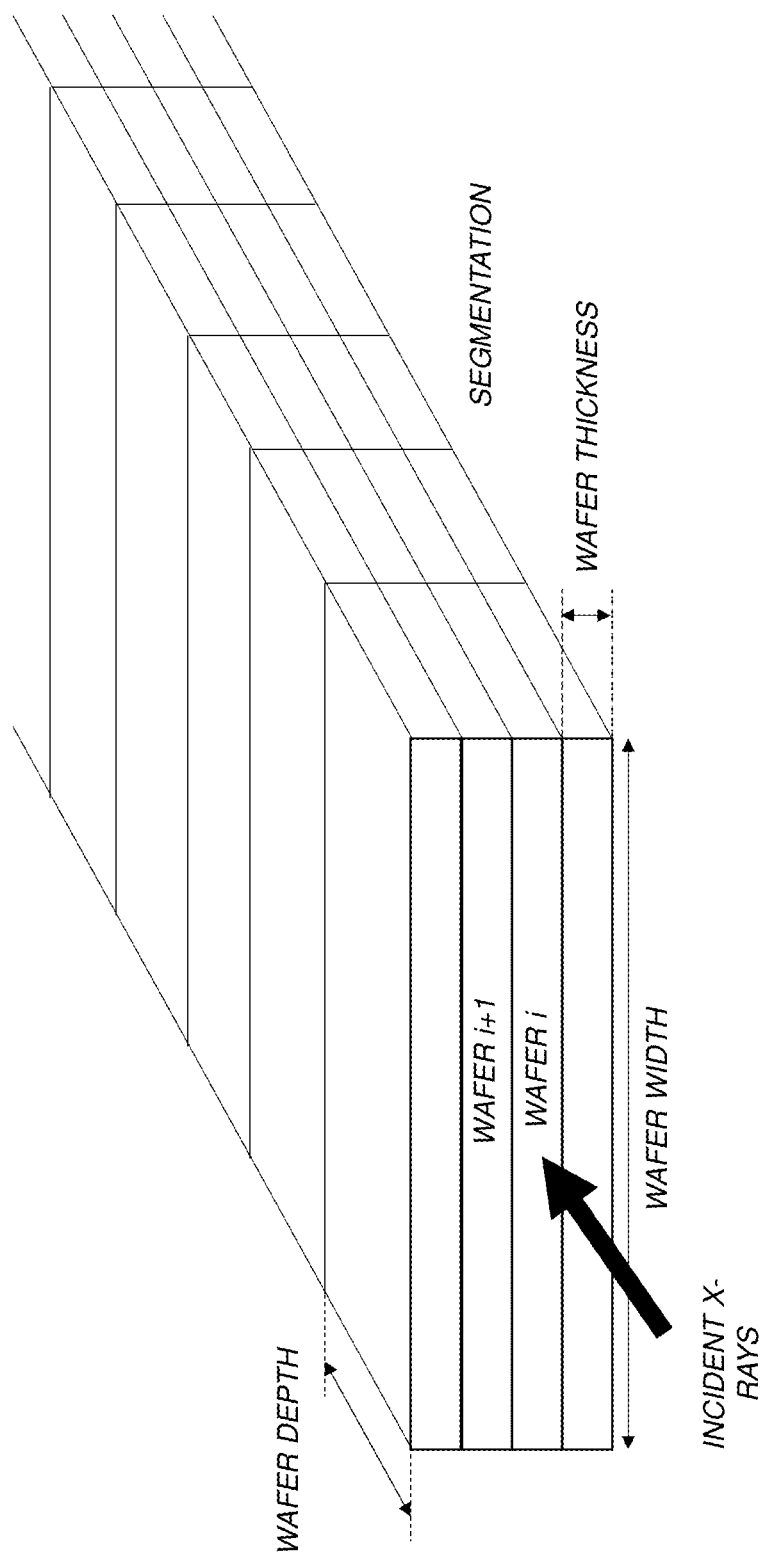
FIG. 6 is a schematic diagram of an edge-on photon-counting detector based on a number of X-ray detector modules or wafers.

As discussed herein, an overall edge-on photon-counting detector may, for example, be based on detector modules typically arranged in groups or sets, also referred to as wafers, see FIG. 6. Such detector modules can then be arranged or stacked one after the other and/or arranged side-by-side in a variety of configurations to form any effective detector area or volume. For example, a full edge-on photon-counting detector for CT applications typically has a total area greater than 200 $cm^2$, which results in a large number of detector modules, such as 1500-2000 detector modules.

By way of example, detector modules may generally be arranged side-by-side and/or stacked, e.g. in a planar or slightly curved overall configuration.

Since the X-ray interactions of incident X-ray photons will be distributed and occurring in different depths along the depth (length) of the detector modules, the overall count rate will be distributed among the pixels in depth. In some embodiments, the pixels may be regarded as being organized in different depth segments depending on the depth of the pixels in relation to the edge of the edge-on photon-counting detection at which the X-rays incident. In this example, the first depth segment is the depth segment closest to the X-ray source. By way of example, over a depth of 40 mm it would be possible to have 400 depth segments or more and the count rate would be correspondingly decreased. The depth is important for dose efficiency and the segmentation protects from pulse pile-up and maintains the spatial resolution of the X-ray imaging system.

In the prior art, the detector modules have often been implemented as so-called Multi-Chip Modules (MCMs) in the sense that the detector modules have semiconductor base substrates for electric routing and for a number of ASICs. The routing will include a connection for the signal from each pixel to an ASIC input as well as connections from the ASICs to external memory and/or digital data processing.

Power to the ASICs may be provided through similar routing taking into account the increase in cross-section, which is required for the large currents in these connections, but the power may also be provided through a separate connection. Hence, in the prior art, each individual pixel is connected to a subsequent ASIC channel where a MCM technology is employed to integrate the ASICs and electric routing on the silicon substrate.

The present invention provides further improvements over prior art X-ray detectors by instead using active integrated pixels in the detector modules. This means that part of the analog processing of the electric signals is moved from the ASICs into the pixels. For instance, moving the pre-amplifying from the ASICs to the pixels lowers the capacitance at the input to the pre-amplifiers since no long traces are needed to route the signal from the pixels to the ASICs. Further advantages of integrating at least part of the analog signal processing in the pixels include smaller pixel sizes, which in turn reduces the power consumption per pixel and enables a reduction of the minimum noise threshold.

In other words, the active integrated pixels may be configured to operate as detector elements and also perform analog processing of the electrical signals of the detector elements.

Figure 7:
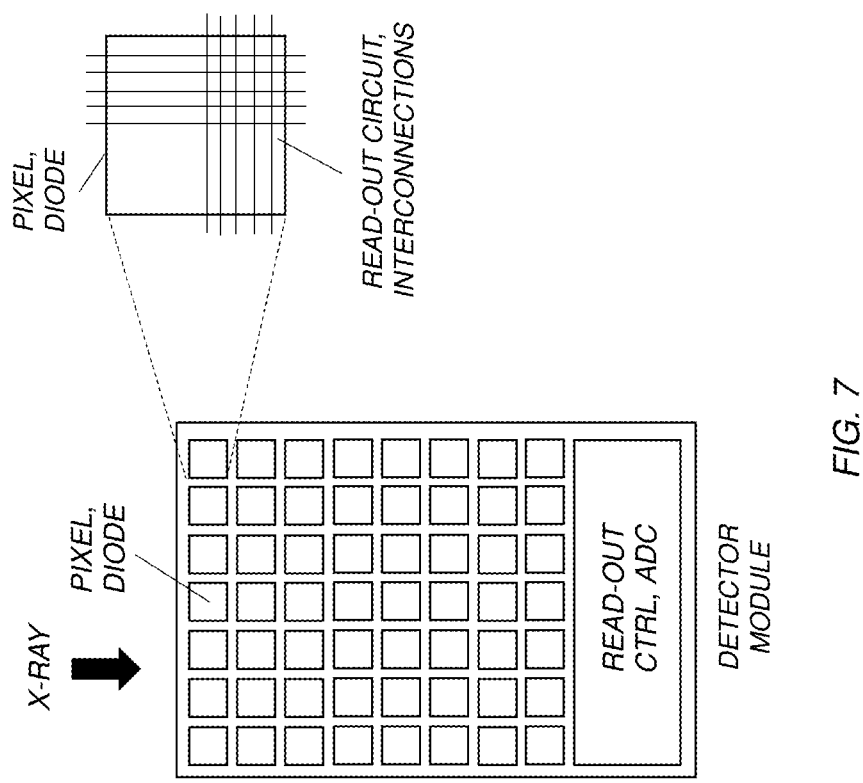
FIG. 7 is a schematic diagram of an X-ray detector module according to an embodiment.

FIG. 7 is a schematic diagram of a detector module, also referred to as a chip, according to an embodiment. The detector module comprises a semiconductor substrate or material comprising a plurality of active integrated pixels arranged in the semiconductor substrate. In a particular embodiment, the plurality of active integrated pixels is arranged at a main side (front side) of the semiconductor substrate in a grid or matrix, or another pattern, as shown in the figure. The main side of the semiconductor is typically perpendicular to the edge facing the X-ray source. The figure also illustrates the arrangement of the pixels in different depth segments with regard to the edge facing the X-ray source and at which X-rays incident on the detector module.

In an embodiment, the detector module also comprises further processing circuitry, such as analog processing circuitry and/or digital processing circuitry, exemplified as read-out circuitry, control circuitry and analog-to-digital conversion (ADC) circuitry in the figure. This further processing circuitry may be implemented in or as one or more ASICs.

The further processing circuitry is advantageously arranged in the semiconductor substrate at the same main side (front side) as the plurality of active integrated pixels. In such a case, the further processing circuitry is preferably arranged at the portion or part of the main side at or in connection with the edge facing away from the X-ray source and the incident X-ray as shown in the figure. This embodiment reduces any dead area of the detector module by reducing the portion of the detector module that is used for the further processing circuitry. In addition, the further processing circuitry is protected from the incoming X-ray by be arranged furthest away from the edge of incidence. Hence, in an embodiment, the at least one detector module comprises an analog processing circuitry and a digital processing circuitry. At least part of the analog processing circuitry is implemented in the plurality of active integrated pixels arranged in the at least one detector module. Any remaining part of the analog processing circuitry and optionally the digital processing circuitry is implemented at a portion of the main side of the semiconductor substrate at or in connection with a respective edge of the at least one detector module opposite to the respective edge facing incident X-rays.

By way of example, the at least one detector module comprises the plurality of active integrated pixels arranged in at least two directions, wherein one of the at least two directions has a component in a direction of the incident X-rays. Alternatively, the plurality of active integrated pixels may be arranged as an array in a direction substantially orthogonal to the direction of the incident x-rays, and each of the active integrated pixels may be oriented edge-on to the incident x-rays.

In an illustrative, but non-limiting, example the area of the semiconductor substrate comprising active integrated pixels may be from 5×5 mm up to 50×50 mm, such as 10×10 mm, 15×15 mm, 20×20 mm, 25×25 mm, 30×30 mm, 35×35 mm, 40×40 mm or 45×45 mm. Also non-quadratic, such as rectangular, areas with active integrated pixels are possible.

In a particular example, at least part of the active integrated pixels have a longer extension in a direction of the incident X-rays than in a direction orthogonal to the direction of the incident X-rays, with a relation of at least 2:1. In other words, the active integrated pixels may be asymmetric in the geometrical design and have at least double the extension (depth) in the direction of the incident X-rays than the extension in a direction orthogonal (perpendicular) to the direction of the incident X-rays.

In FIG. 6, each wafer may comprise one detector module or may comprise multiple detector modules. In the latter case, the detector modules may be attached to a thin substrate, such as a ceramic substrate, to form a wafer that can be handled as a single unit. Purely as an example, the width of the wafer may be in order of 25-50 mm, and the depth of the wafer may be in the same order of 25-50 mm, whereas the thickness of the wafer may be in the order of 300-900 µm.

Figure 8:
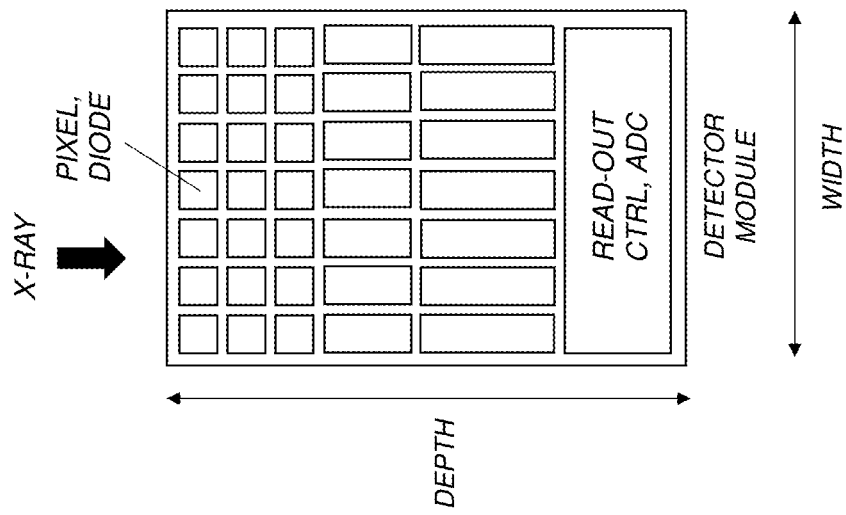
FIG. 8 is a schematic diagram of an X-ray detector module according to an embodiment.

FIG. 7 schematically also indicates an active integrated pixel with a so-called detector diode (electrode) together with read-out electronics and interconnections. Each such active integrated pixel typically has a size in the µm range. In an embodiment, the active integrated pixels are quadratic and typically all active integrated pixels in a detector module have the same shape and size. It is, however, possible to use other shapes for the pixels, such as rectangular, and/or having active integrated pixels with different sizes and/or shapes in the same detector module as shown in FIG. 8. In FIG. 8 the active integrated pixels have the same width but different depths. For instance, the depth of the active integrated pixels may increase for different depth segments and is thereby based on the distance to the edge at which the X-rays incident on the detector module. This means that the active integrated pixels at this edge preferably have smaller depth as compared to active integrated pixels closest to the opposite edge. In such an embodiment, the detector modules may include active integrated pixels having two or more different depths. In other words, the plurality of active integrated pixels has a same width and a depth that is dependent on a distance between an active integrated pixel in the grid or matrix and the edge of the detector module facing incident X-rays.

Figure 15:
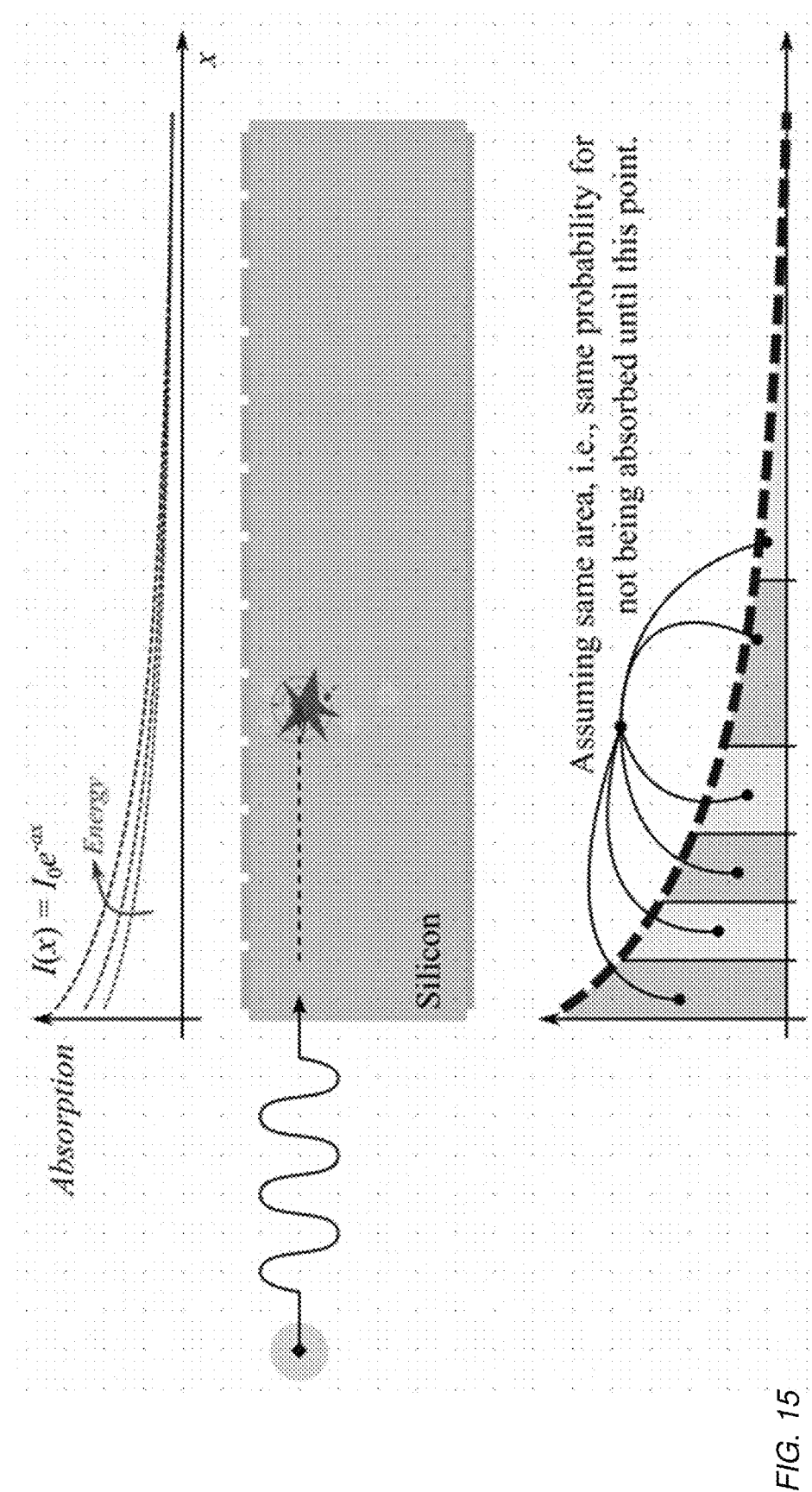
FIG. 15 schematically illustrates the concept of using increasing pixel sizes along the depth direction of the edge-on photon-counting detector.

Different pixel depths, and in particular pixel depth as a function of depth segment or distance to the edge at which the X-rays incident on the detector module can be used to tailor the probabilities or likelihoods for detecting an event at an active integrated pixel. FIG. 15 schematically illustrates this concept by showing the absorption at different depths of the detector module. As is shown in the upper panel, an incoming photon is more likely to trigger an event in an active integrated pixel close to the edge (x=0) as compared to an active integrated pixel further from the edge. The indicates that by assuming the same probability for a photon to not being absorbed in the semiconductor substrate at a particular point, which corresponds to the same areas under the curve, then the depths of the active integrated pixels need to increase for increasing x, i.e., depths of the detector module.

Figure 9:
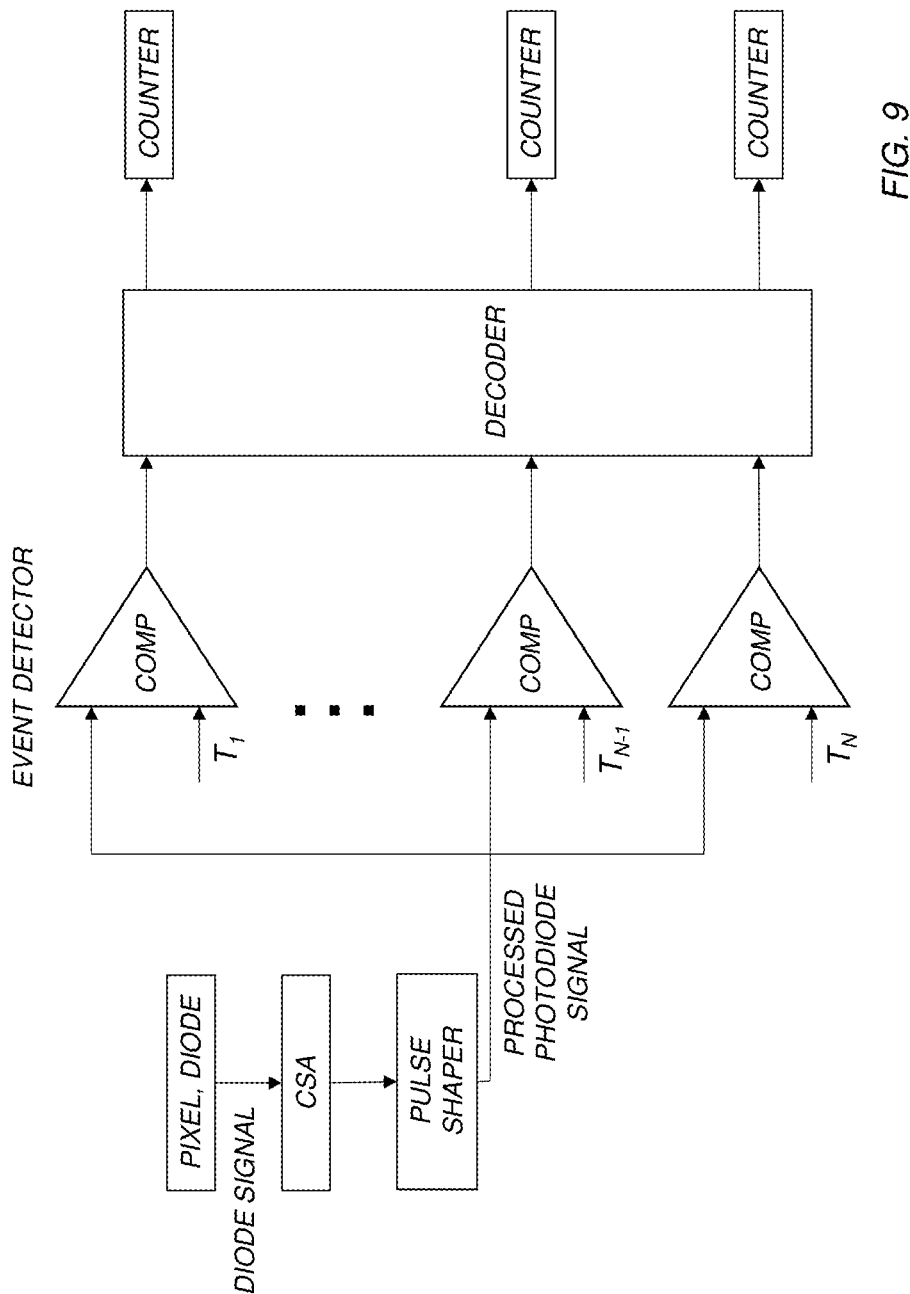
FIG. 9 is a schematic diagram of processing of the diode signal according to an embodiment.

In general, the X-ray photons, including also photons after Compton scattering, are converted to electron-hole pairs inside the semiconductor substrate of the detector modules, where the number of electron-hole pairs is generally proportional to the photon energy. The electrons and holes are drifting towards the active integrated pixels, then leaving the photon-counting detector. During this drift, the electrons and holes induce an electrical current in the active integrated pixels, a current which may be measured, e.g., through a Charge Sensitive Amplifier (CSA), followed by a Pulse Shaper, also referred to as Shaping Filter (SF), as schematically illustrated in FIG. 9.

In more detail, the incoming X-ray photons may interact with the semiconductor substrate of the detector modules either through the photoelectric effect or Compton interaction. Compton interaction, also referred to as Compton scattering, is the scattering of a photon by a charged particle, usually an electron. It results in a decrease in energy of the photon, called the Compton effect. Part of the energy of the photon is transferred to the recoiling electron. The photon may be involved in multiple Compton interactions during its path through the semiconductor substrate. As a consequence of this Compton interaction, there will be diffusion and/or distribution of charge in the semiconductor substrate.

More specifically, an X-ray photon may create a secondary electron through Compton interaction or photo effect. The electron will get kinetic energy from the X-ray photon and move a short distance, e.g., 1 µm-50 µm, and during its path will excite electron-hole pairs. Every electron hole pair will cost about 3.6 eV to create, which means that, for example, a Compton interaction with 15 keV deposited energy to the electron will create around 4200 electron-hole pairs, forming a so-called charge cloud. The charge cloud will move according to the electric field lines and if the back side of the detector module is biased positive the holes will move towards the readout electrodes, i.e., active integrated pixels, arranged on the front side of the detector module or and the electrons will move towards the back side. The readout electrodes are functioning as detector elements or pixels, on the front side of the detector module. By way of example, the voltage on the back side may be around 200 V, as an illustrative, but non-limiting, example, and virtual ground on the front side.

As the number of electrons and holes from one X-ray event is proportional to the X-ray energy, the total charge in one induced current pulse is proportional to this energy. The current pulse, also referred to as diode signal, is amplified in the CSA and then filtered by the pulse shaper. By choosing an appropriate shaping time of the pulse shaper, the pulse amplitude after filtering is proportional to the total charge in the current pulse, and therefore proportional to the X-ray energy. Following the pulse shaper, the pulse amplitude is measured by comparing its value with one or several threshold values ($T_1$-$T_N$) in one or more comparators (COMP), and counters are introduced by which the number of cases when a pulse is larger than the threshold value may be recorded. In this way it is possible to count and/or record the number of X-ray photons with an energy exceeding an energy corresponding to respective threshold value ($T_1$-$T_N$), which has been detected within a certain time frame.

When using several different threshold values, a so-called energy-discriminating photon-counting detector is obtained, in which the detected photons can be sorted into energy bins corresponding to the various threshold values. Sometimes, this type of photon-counting detector is also referred to as a multi-bin detector. In general, the energy information allows for new kinds of images to be created, where new information is available and image artifacts inherent to conventional technology can be removed. In other words, for an energy-discriminating photon-counting detector, the pulse heights are compared to a number of programmable thresholds ($T_1$-$T_N$) in the comparators and classified according to pulse-height, which in turn is proportional to energy.

However, an inherent problem in any CSA is that it will add electronic noise to the detected current. In order to avoid detecting noise instead of real X-ray photons, it is therefore important to set the lowest threshold value high enough so that the number of times the noise value exceeds the threshold value is low enough not to disturb the detection of X-ray photons.

By setting the lowest threshold above the noise floor, electronic noise, which is the major obstacle in the reduction of radiation dose of the X-ray imaging systems, can be significantly reduced The pulse shaper has the general property that large values of the shaping time will lead to a long pulse caused by the X-ray photon and reduce the noise amplitude after the filter. Small values of the shaping time will lead to a short pulse and a larger noise amplitude. Therefore, in order to count as many X-ray photons as possible, a large shaping time is desired to minimize noise and allowing the use of a relatively small threshold level.

The values of the set or table of thresholds, by which the pulse heights are compared in the comparators, affect the quality of the image data generated by the edge-on photon-counting detector. Furthermore, these threshold values are temperature dependent. Therefore, in an embodiment, calibration data generated by power-consuming circuitries in the edge-on photon-counting detector may be used to set thresholds ($T_1$-$T_N$).

According to the present invention all or part of the analog signal processing illustrated in FIG. 9 is integrated into the pixels to thereby form so-called active integrated pixels.

An aspect of the invention relates to an edge-on photon-counting detector. The edge-on photon-counting detector comprises at least one detector module having a respective edge facing incident X-rays. The at least one detector module comprises a semiconductor substrate. The edge-on photon-counting detector also comprises a plurality of active integrated pixels arranged in the semiconductor substrate.

In an embodiment, the edge-on photon-counting detector comprises multiple such detector modules arranged side-by-side and/or stacked.

The edge-on photon-counting detector is typically fabricated based on silicon as semiconductor material for the detector modules.

To compensate for the low stopping power of silicon, the detector modules are typically oriented in edge-on geometry with their edge directed towards the X-ray source as shown in FIGS. 4-5, 7-8, thereby increasing the absorption thickness. In order to cope with the high photon fluxes in clinical CT, a segmented structure of the active integrated pixels into depth segments is preferably applied, which is achieved by implanting individual active integrated pixels in depth segments on the silicon substrate as shown in FIGS. 4-5, 7-8.

In a particular embodiment, the semiconductor substrate is made of float zone (FZ) silicon. FZ silicon is very pure silicon obtained by vertical zone melting. In the vertical configuration, molten silicon has sufficient surface tension to keep the charge from separating. Avoidance of the necessity of a containment vessel prevents contamination of the silicon. Hence, the concentrations of light impurities in the FZ silicon are extremely low. The diameters of FZ silicon wafers are generally not greater than 200 mm due to the surface tension limitations during growth. A polycrystalline rod of ultra-pure electronic grade silicon is passed through an RF heating coil, which creates a localized molten zone from which the crystal ingot grows. A seed crystal is used at one end in order to start the growth. The whole process is carried out in an evacuated chamber or in an inert gas purge. The molten zone carries the impurities away with it and, hence, reduces impurity concentration. Specialized doping techniques like core doping, pill doping, gas doping and neutron transmutation doping may be used to incorporate a uniform concentration of impurity.

The semiconductor substrate is, in an embodiment, made of high resistivity silicon, such as high resistivity FZ silicon. As used herein, high resistivity silicon is defined as monocrystalline silicon having a bulk resistivity larger than 1 kΩcm.

The plurality of active integrated pixels may be implemented as active integrated Complementary Metal Oxide Semiconductor (CMOS) pixels in the semiconductor substrate. Hence, the analog circuitry of the active integrated pixels may be produced using CMOS technology.

As shown in FIG. 2 and further discusses above, the edge-on photon-counting detector 20 may comprise an analog processing circuitry 25 and a digital processing circuitry 40. According to an embodiment, at least part of the analog processing circuitry 25 is implemented in the plurality of active integrated pixels. Any remaining part of the analog processing circuitry 25 is implemented in at least one ASIC optionally also comprising the digital processing circuitry 40 or a portion thereof. This at least one ASIC is, in an embodiment, arranged in the at least one detector module of the edge-on photon-counting detector 20.

FIGS. 10 to 13 illustrate various embodiments of such active integrated pixels with different analog read-out electronics in the pixels. In these figures, the current generating part of the pixel is illustrated as a diode outputting a current pulse or diode signal.

FIG. 10 illustrates an embodiment of an active integrated pixel comprising an amplifier configured to generate an output signal based on a current pulse generated by the active integrated pixel or diode. In an embodiment, the amplifier is a charge sensitive amplifier (CSA) configured to integrate the current pulse into a voltage signal.

The output signal, such as voltage signal, from the amplifier, preferably CSA, is in this embodiment routed to external processing circuitry arranged in the semiconductor substrate in the detector module, such as in the form of one or more ASICs, see read-out, ctrl and ADC in FIGS. 7 and 8.

With an increased number of active integrated pixels in the detector module the count rate per pixel decreases and also the noise requirements are relaxed. This implies that amplifiers with comparatively low power consumption and low bandwidth can be used in the active integrated pixels. Furthermore, single-ended amplifiers are preferred due to the nature of the diode. This further allows for less complex amplifiers. The lower diode capacitance, the input referred noise from the amplifier will be less dominant as compared to using larger pixel sizes.

FIG. 11 illustrates another embodiment of an active integrated pixel. This embodiment comprises a pulse shaper, also referred to as shaping filter, in addition to the amplifier. This pulse shaper is configured to filter the output signal from the amplifier.

The current pulse from the diode is preferably integrated using a CSA. Typically, this generates a slow-moving voltage at the output of the CSA. To compensate for this behavior a cancellation circuit (CC), such as a pole-zero cancellation circuit, is preferably arranged connected to the CSA and the pulse shaper. This pole-zero CC cancels or at least suppresses the slow response of the CSA with maintained charge/current integration. Accordingly, the time constant will instead be determined by the shaper integration time of the pulse shaper.

The output signal from the pulse shaper is in this embodiment routed to external processing circuitry arranged in the semiconductor substrate in the detector module, such as in the form of one or more ASICs, see read-out, ctrl and ADC in FIGS. 7 and 8.

Figure 12:
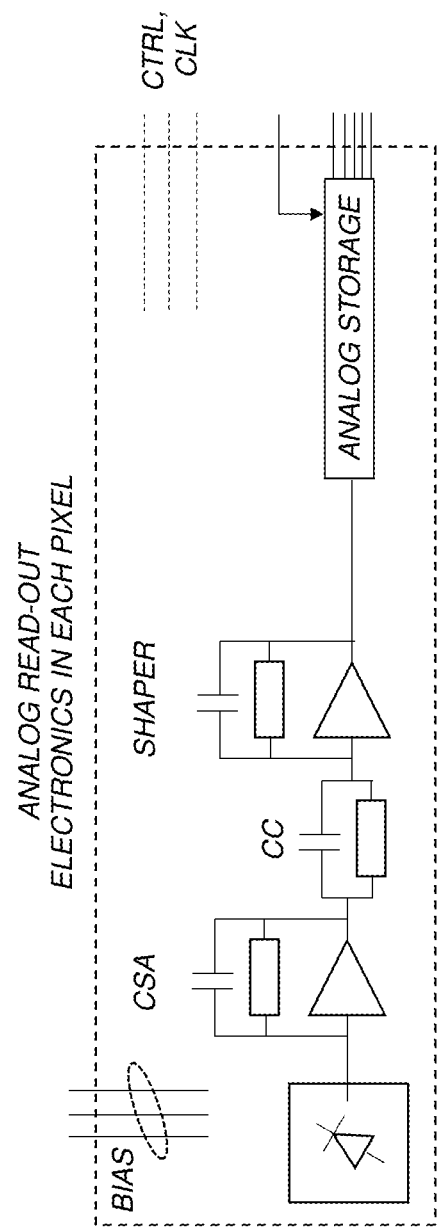
FIG. 12 is a schematic diagram of an active integrated pixel according to a further embodiment.

FIG. 12 illustrates a further embodiment of an active integrated pixel. This embodiment comprise an analog storage connected to, and arranged downstream of, the pulse shaper. This analog storage could be implemented in the active integrated pixel to at least temporarily store and retain the output signal from the pulse shaper. This enables controlled read-out of data from the active integrated pixel and the analog storage, such as based on a control signal (ctrl) and or at scheduled time instances, such as controlled based on a clock signal (clk).

An analog storage as shown in FIG. 12 may also be used in an embodiment as shown in FIG. 10, i.e., without any pulse shaper. In such a case, the analog storage is connected to the amplifier (CSA) or connected to the amplifier (CSA) through the pole-zero CC.

Figure 13:
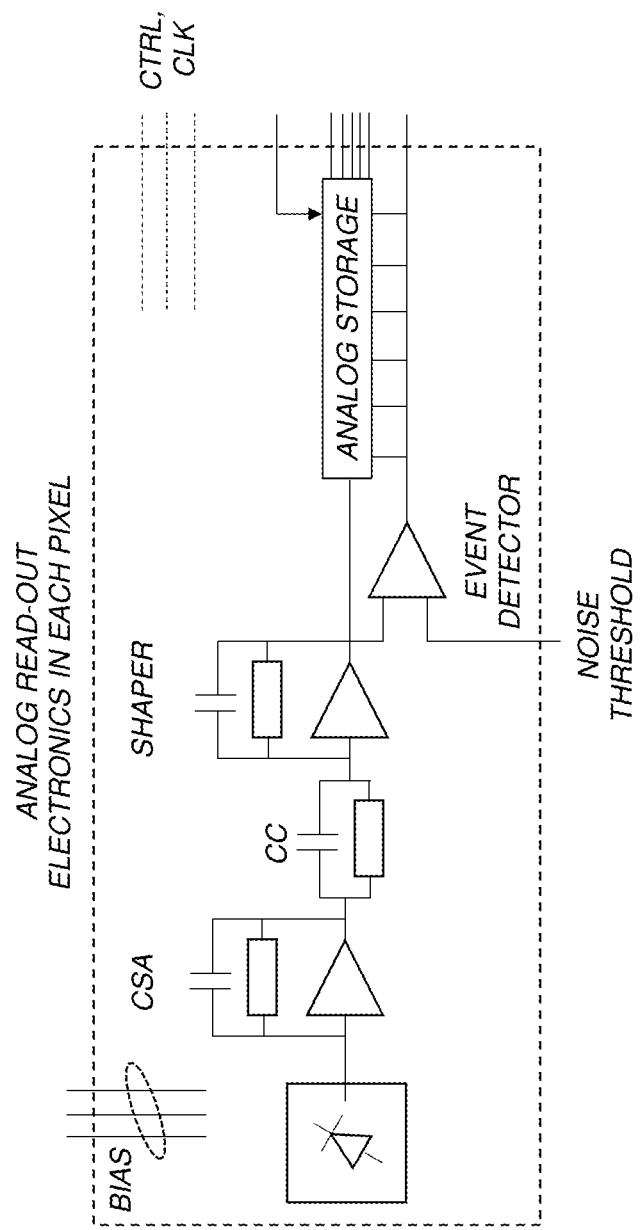
FIG. 13 is a schematic diagram of an active integrated pixel according to yet another embodiment.

In yet another embodiment as shown in FIG. 13, the pixel comprises an event detector represented as a comparator in the figure. This event detector is then configured to detect a photon event by comparing a pulse amplitude of the output signal from the pulse shaper with a threshold value, represented by a noise threshold in the figure.

In a particular embodiment, the event detector is configured to generate a trigger signal based on the comparison of the pulse amplitude with the threshold value, and preferably generates the trigger signal if the pulse amplitude is equal to or exceeds, or exceeds, the threshold value.

In this embodiment, read-out of the analog storage may be controlled by the trigger signal output by the event detector. Thus, read-out of the data in the analog storage then takes place preferably only when the event detector confirms detection of a photon event by the active integrated pixel as represented by having a pulse amplitude (equal to or) above a noise floor as represented by the noise threshold.

In other words, a comparator acting as an event detector can be used to signal to read-out circuitry, typically arranged externally relative to the active integrated pixel, see read-out in FIGS. 7 and 8. For instance, the read-out circuitry could be comprised in the previously mentioned digital processing 30 circuitry. This read-out circuitry reads the analog storage based on the trigger signal from the event detector. The read data may then be further processed, such as compared to thresholds ($T_1$-$T_N$), see FIG. 9, and/or digitized in an ADC, see FIGS. 7 and 8.

If no read-out of the data in the analog storage is performed, the data therein may be consecutively flushed, such as by operating in a first-in-first-out (FIFO) manner. This allows for an asynchronous read out of the data from the analog storage and thereby a reduction in the power consumption during read out.

The trigger signal from the event detector may also be fed to neighboring active integrated pixels in the detector module to trigger them to store data that may then be read out and further processed. This enables detection of properties of the data even through the noise thresholding is not passed.

In another embodiment, read out of the analog storage is performed based on not only a trigger signal from the event detector in the active integrated pixel but also from a respective trigger signal from at least one neighboring active integrated pixel in the detector module.

In an embodiment, all detector modules in the edge-on photon-counting detector comprise active integrated pixels. In such a case, all the active integrated pixels can be of a same type or pixel implementation, i.e., comprise the same or corresponding processing circuitry, such as according to any of the above described and in FIGS. 10 to 13 shown embodiments. In another embodiment, different detector modules in the edge-on photon-counting detector could have different types or implementation of active integrated pixels. For instance, at least one of the detector modules in the edge-on photon-counting detector could comprise active integrated pixels according to a first pixel implementation, such as one of the above described and in FIGS. 10 to 13 shown embodiments, whereas at least one other detector module in the edge-on photon-counting detector could comprise active integrated pixels according to a second, different pixel implementation, such as another of the above described and in FIGS. 10 to 13 shown embodiments. In such a case, active integrated pixels in different detector modules may include different processing circuitries.

It is also possible to have an edge-on photon-counting detector comprising at least one detector module comprising active integrated pixels and at least one detector module comprising traditional pixels, where the processing circuitry is present outside of the pixels, such as in one or more ASICs. For instance, detector modules in a central portion of the edge-on photon-counting detector, which are more likely to capture incident X-ray radiation having passed through an object or patient, could comprise active integrated pixels, whereas peripheral detector modules of the edge-on photon-counting detector could comprise traditional pixels. Generally, the central portion of the edge-on photon-counting detector is more likely to capture incident X-ray radiation having passed through the object or patient and is thereby typically more important in terms of accuracy since it will be involved in generating detection data to be used for imaging the object or patient. Peripheral portions of the edge-on photon-counting detector are less likely to capture X-rays having passed through the object or patient and thereby the accuracy in those portions of the edge-on photon-counting detector may be lower than the accuracy in the central portion and still achieving overall acceptable imaging accuracy for the edge-on photon-counting detector.

Figure 17:
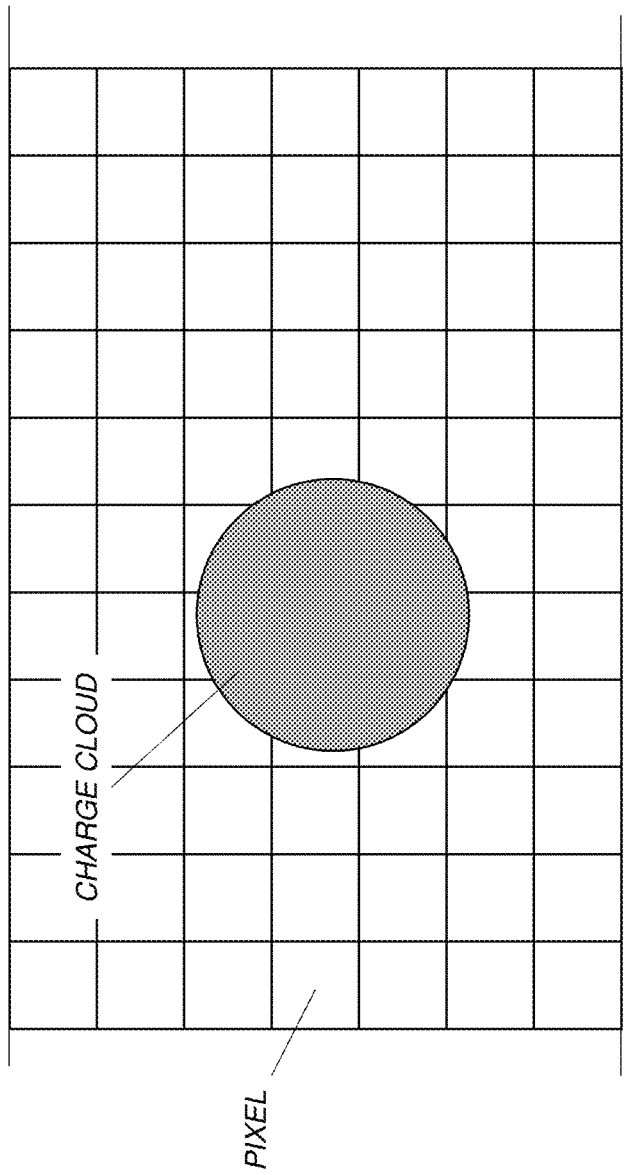
FIG. 17 schematically illustrates portion of a detector module together with a charge cloud to be resolved.

FIG. 17 is a schematic diagram illustrating some active integrated pixels of a detector module. In this example, the active integrated pixels are generally smaller than a charge diffusion represented by the charge cloud to be resolved. For example, the charge cloud may have a width in the order of 100 µm, and the active integrated pixels, or at least a portion thereof, are therefore normally designed to be smaller or even considerably smaller than that. Hence, an X-ray photon traveling through the semiconductor substrate typically results in a charge cloud covering multiple neighboring active integrated pixels in the detector module. This means that a single X-ray photon will most likely trigger event detection in multiple active integrated pixels. In an embodiment, read out of data from the analog storage may therefore be conditioned on detection of an event in multiple neighboring active integrated pixels and thereby on the generation of trigger signals in these active integrated pixels.

For instance, read out of the analog storage is performed when event detectors in at least N neighboring active integrated pixels generate and output a trigger signal within a trigger interval. As an example, most of the active integrated pixels in the detector modules in FIGS. 7 and 8, excluding the edge pixels, have 8 neighboring active integrated pixels. In such a case, read out of the analog storage of a current active integrated pixel can be conditioned upon generation of trigger signals in, for instance, at least 2, at least 3 or at least 4 of the 8 neighboring active integrated pixels within a defined period of time prior to or after, or after, generation of the trigger signal in the current active integrated pixel.

A further solution to reduce the total power consumption of the active integrated pixels in a detector module is to let at least a portion of the analog circuitry implemented therein enter a low-power sleep mode following an event detection by the event detector. For instance, the amplifier (CSA) of an active integrated pixel can temporarily enter a low-power sleep mode based on the trigger signal from the event detector. This low-power sleep mode may then run for a predefined period of time after which the amplifier (CSA) once more enters the normal operation mode.

A reason for powering down amplifiers is that once the active integrated pixel has captured an electric signal and detected it as an event, there is generally a low probability that the same active integrated pixel will anew detect an event within the predefined period of time.

Figure 14:
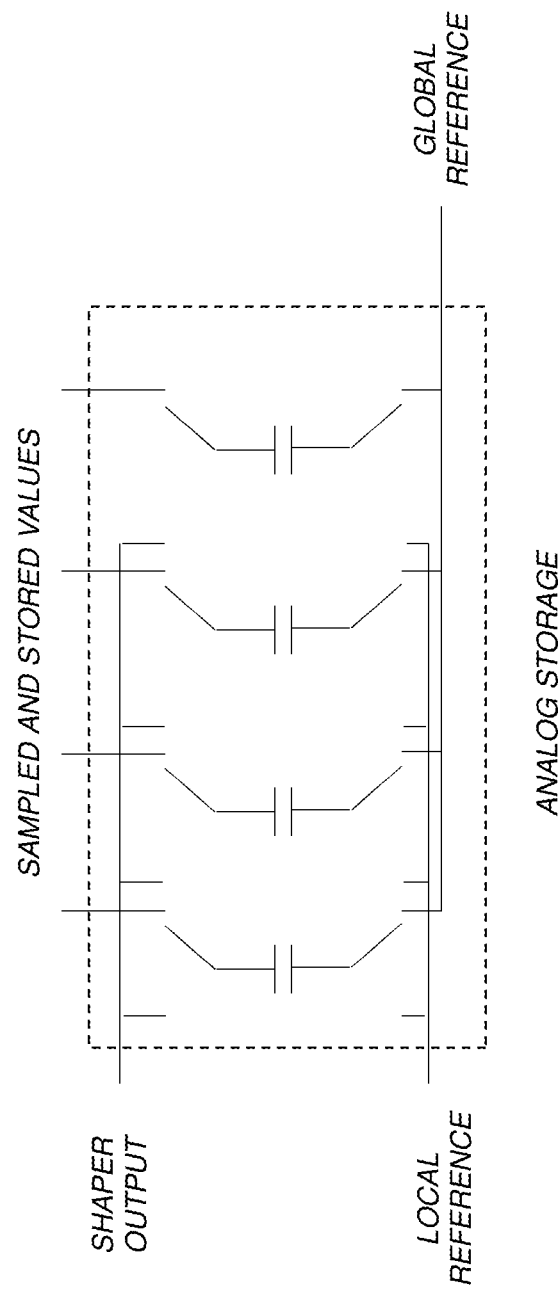
FIG. 14 is a schematic diagram of an analog storage according to an embodiment.

FIG. 14 is a schematic diagram illustrating an implementation example of an analog storage. The figure indicates the output from the pulse shaper together with output of stored data or values from the analog storage. In an embodiment, in order to reduce any impact of global vs. local references or ground, the voltage can be stored differentially using the shaper output and its local reference, which, for instance, may be a local offset that is optionally individually tuned for each active integrated pixel. Then, when values are read from the analog storage, the voltage difference across the capacitor is sensed using the global reference, which may, for instance, be global ground for the active integrated pixels.

Figure 16:
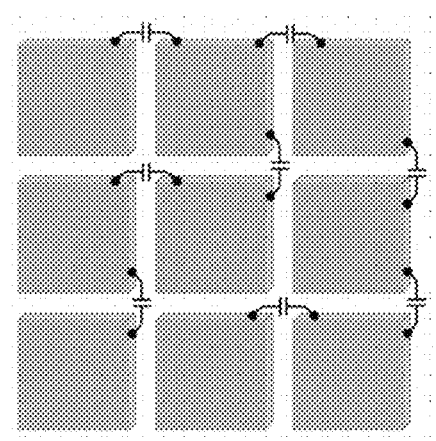
FIG. 16 partially illustrates diode-to-diode capacitance between the active integrated pixels.

FIG. 16 illustrates the effect of placing many small diodes near each other as a result of having many small active integrated pixels close to each other in the detector module. The illustrated diode-to-diode capacitances dominate, when the diodes become smaller and smaller, the parasitic capacitance seen at the input of the amplifier (CSA). Thus, once the pixel dimensions decrease the sidewall capacitance between the diodes (active integrated pixels) do not decrease by the same amount as the bottom-top capacitances of the diodes. The required input-referred noise of the analog front-end increases with increased capacitance. Noise performance is improved with higher power consumption and in order to keep the power consumption low, the capacitances are preferable minimized.

The implementation of at least part of the analog circuitry into the pixels to form active integrated pixels enables a reduction in size of the pixels as compared to prior art solutions. This small size of the active integrated pixels allows multiple active integrated pixels in a detector module to detect a charge cloud generated by a single X-ray photon as shown in FIG. 17. This in turn enables the X-ray imaging system comprising the edge-on photon-counting detector to determine an estimate of charge diffusion originating from a Compton interaction or an interaction through photo effect related to the X-ray photon in a particular detector module of the edge-on photon-counting detector.

The estimation of charge diffusion can in turn be used for further processing. For instance, the initial point of interaction along the thickness of the detector module can be estimated based at least partly on the determined estimate of charge diffusion by the X-ray imaging system. Furthermore, the determined estimate of charge diffusion can be used to provide a significantly improved estimate of the point of interaction of the incident X-ray photon in the detector module.

By way of example, it may be possible to determine an estimate of a distance, along the thickness of the detector module, between the point of detection of the X-ray photon in the detector module and the initial point of interaction between the X-ray photon and the semiconductor substrate based on the determined estimate of charge diffusion, and then determine an estimate of the initial point of interaction based on the point of detection and the determined estimate of a distance along the thickness of the detector module. The thickness of the detector module generally extends in the direction of diffusion between the back side and front side of the detector module. In particular, the shape, and in particular, the width of the charge diffusion is measured or estimated, and the distance between the point of detection and the initial point of interaction is determined based on the shape or width of the charge diffusion or distribution.

In another example, information about the charge diffusion may be used by the X-ray imaging system for providing improved resolution of an initial point of interaction between an X-ray photon and a detector module in at least one of the two directions over which the active integrated pixels are distributed on the main (front) side of the detector module. For example, increased resolution may be obtained based on information of a charge cloud profile in one or both of these directions. The considered direction(s) may include the width direction and/or depth direction of the detector module or wafer as indicated in FIG. 6.

It may also be desirable, as an alternative or a complement, to estimate the initial point of interaction along the thickness of the detector module based at least partly on the determined estimate of charge diffusion as mentioned above.

Accordingly, it has been shown that information about charge diffusion may be used to improve the resolution in at least one of three directions of a detector module in an edge-on photon-counting detector comprising active integrated pixels.

A further aspect of the invention relates to an X-ray imaging system comprising an edge-on photon-counting detector according to the embodiments. The X-ray imaging system is, in an embodiment, a CT system. In an embodiment, the X-ray imaging system also comprises an X-ray source and optionally an image processing system.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible.

The invention claimed is:

1. An edge-on photon-counting detector comprising:
at least one detector module having a respective edge facing incident X-rays, the at least one detector module comprising a semiconductor substrate; and
a plurality of active integrated pixels arranged in the semiconductor substrate, the plurality of active integrated pixels being one of: (i) arranged in at least two directions, one of the at least two directions having a component in a direction of the incident X-rays, and (ii) arranged as an array in a direction substantially orthogonal to the direction of the incident x-rays, with each of the active integrated pixels being oriented edge-on to the incident x-rays,
wherein the active integrated pixels are configured to operate as detector elements configured to detect electrical current induced from one or more of drifting electrons and holes in the semiconductor substrate, the active integrated pixels being configured to perform analog processing of electrical signals of the detector elements, and
wherein at least one of the active integrated pixels comprises
an amplifier configured to generate an output signal based on a current pulse generated by the active integrated pixel, and
an analog storage downstream of the amplifier to enable controlled read-out of data from the active integrated pixel and the analog storage.

2. The edge-on photon-counting detector according to claim 1, further comprising an analog processing circuitry, at least part of the analog processing circuitry being implemented in the plurality of active integrated pixels, any remaining part of the analog processing circuitry being implemented in at least one application-specific integrated circuit (ASIC disposed in the at least one detector module.

3. The edge-on photon-counting detector according to claim 1, wherein the plurality of active integrated pixels is disposed on a main side of the semiconductor substrate in a grid or matrix.

4. The edge-on photon-counting detector according to claim 3, wherein the plurality of active integrated pixels has a same width and a depth that is dependent on a distance between an active integrated pixel in the grid or matrix and the respective edge facing incident X-rays.

5. The edge-on photon-counting detector according to claim 3, wherein an area of the semiconductor substrate comprising the plurality of active integrated pixels is selected within an interval of 5×5 mm to 50×50 mm.

6. The edge-on photon-counting detector according to claim 1, wherein the at least one detector module comprises an analog processing circuitry, at least part of the analog processing circuitry being implemented in the plurality of active integrated pixels, any remaining part of the analog processing circuitry being implemented at a portion of the main side of the semiconductor substrate at or in connection with a respective edge of the at least one detector module opposite to the respective edge facing incident X-rays.

7. The edge-on photon-counting detector according to claim 1, wherein at least a portion of the plurality of active integrated pixels comprises an amplifier configured to generate an output signal based on a current pulse generated by the respective active integrated pixel.

8. The edge-on photon-counting detector according to claim 7, wherein the at least a portion of the plurality of active integrated pixels comprises a pulse shaper configured to filter the output signal from the amplifier, and/or wherein the at least a portion of the plurality of active integrated pixels comprises a cancellation circuit (CC) connected to the amplifier and the pulse shaper.

9. The edge-on photon-counting detector according to claim 8, wherein the at least a portion of the plurality of active integrated pixels comprises an analog storage connected to and disposed downstream of the pulse shaper and configured to at least temporarily store and retain an output signal from the pulse shaper.

10. The edge-on photon-counting detector according to claim 9, wherein the at least a portion of the plurality of active integrated pixels comprises an event detector configured to:
  detect a photon event by comparing a pulse amplitude of an output signal from the pulse shaper with a threshold value, and
  generate a trigger signal when the pulse amplitude is equal to or exceeds the threshold value.

11. The edge-on photon-counting detector according to claim 10, wherein read-out of data in the analog storage is controlled by the trigger signal output by the event detector, and/or
  wherein read-out of data in the analog storage is performed based on the trigger signal from the event detector in the active integrated pixel and based on a respective trigger from at least one neighboring active integrated pixel in the at least one detector module.

12. The edge-on photon-counting detector according to claim 10, wherein the edge-on photon counting detector further comprises digital processing circuitry comprising read-out circuitry configured to read out data from the analog storage based on the trigger signal from the event detector, and/or
  wherein the amplifier is configured to enter a low-power sleep mode based on the trigger signal from the event detector.

13. The edge-on photon-counting detector according to claim 1, wherein the semiconductor substrate is made of silicon selected from the group consisting of float zone (FZ) silicon, high resistivity silicon and high resistivity FZ silicon, the high resistivity silicon and the high resistivity FZ silicon having a bulk resistivity larger than 1 kΩcm.

14. The edge-on photon-counting detector according to claim 1, wherein the at least one detector module comprises a plurality of detector modules having a respective edge facing incident X-rays and arranged side-by-side and/or stacked.

15. The edge-on photon-counting detector according to claim 14, wherein the plurality of detector modules are attached to the semiconductor substrate to form a wafer, the wafer having a width selected within an interval of 25 mm to 50 mm, a depth selected within an interval of 25 mm to 50 mm, and a thickness selected within an interval of 300 μm to 900 μm.

16. The edge-on photon-counting detector according to claim 1, wherein the plurality of active integrated pixels is implemented as active integrated Complementary Metal Oxide Semiconductor (CMOS) pixels in the semiconductor substrate.

17. The edge-on photon-counting detector according to claim 1, wherein a least part of the active integrated pixels have a longer extension in a direction of the incident X-rays than in a direction orthogonal to the direction of the incident X-rays, with a relation of at least 2:1.

18. An X-ray imaging system comprising:
  the edge-on photon-counting detector according to claim 1.

19. The X-ray imaging system according to claim 18, wherein the X-ray imaging system is a computed tomography (CT) system.

20. The X-ray imaging system according to claim 18, wherein the X-ray imaging system is configured to estimate a charge diffusion originating from a Compton interaction or an interaction through photo effect related to an X-ray photon in a detector module, and the X-ray imaging system is configured to estimate an initial point of interaction between the X-ray photon and the at least one detector module along a thickness of the at least one detector module based on the estimated charge diffusion.

21. The X-ray imaging system according to claim 20, wherein the X-ray imaging system is configured to use information about the charge diffusion to increase a resolution of an initial point of interaction between the X-ray photon and the at least one detector module in at least one of two directions over which the plurality of active integrated pixels are distributed on a main side of the detector module.

22. The X-ray imaging system according to claim 20, wherein
  the charge diffusion is represented by a charge cloud, and
  at least a portion of the plurality of active integrated pixels has a size that is smaller than the charge cloud.

* * * * *